United States Patent
Buzas et al.

Patent Number: 4,983,614
Date of Patent: Jan. 8, 1991

[54] BENZHYDRYLOXYETHYLPIPERIDINE DERIVATIVES, PROCESS FOR THEIR PREPARATION AND PHARMACEUTICAL COMPOSITIONS, IN WHICH THEY ARE PRESENT

[75] Inventors: André Buzas, Bievres; Jean-Yves Merour; Roland Ollivier, both of Olivet, all of France

[73] Assignee: Les Laboratoires Meram, Paris, France

[21] Appl. No.: 291,189

[22] Filed: Dec. 28, 1988

Related U.S. Application Data

[63] Continuation of Ser. No. 92,072, Sep. 2, 1987, abandoned.

[30] Foreign Application Priority Data

Sep. 5, 1986 [FR] France ................. 86 12508

[51] Int. Cl.$^5$ .......................... A61K 31/445
[52] U.S. Cl. ..................... 514/317; 514/330; 546/227; 546/239
[58] Field of Search ............ 546/227, 239; 514/317, 514/330

[56] References Cited

U.S. PATENT DOCUMENTS 4,096,259  6/1978  Buzas et al. ................. 514/255
4,433,152  2/1984  Muramatsu et al. .......... 546/227

FOREIGN PATENT DOCUMENTS 1014668  12/1965  United Kingdom ............ 546/227

OTHER PUBLICATIONS

Vejdelek et al., "Potential Antiparkinsonic Agents: Synthesis and, etc.," C.A. 103(5), 37334h, Aug. 1985.
M. Nakanishi et al., Chemical Abstracts, vol. 63, 13224f,g, (1965).

Goodman and Gilman, The Pharmacological Basis of Therapeutics, 6th Ed., pp. 484–487, (1980).

Primary Examiner—Glennon H. Hollrah
Attorney, Agent, or Firm—Poms, Smith, Lande & Rose

[57] ABSTRACT

The invention relates to benzhydryloxyethylpiperidine derivatives corresponding to one of the formulae below:

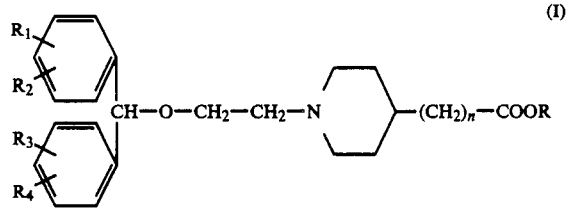

(I)

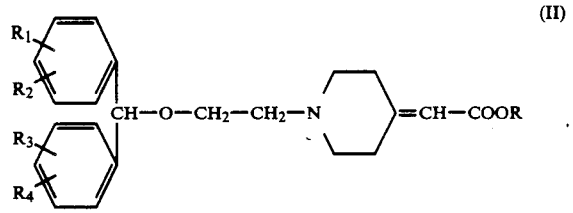

(II)

in which:

$R_1$, $R_2$, $R_3$ and $R_4$, which are identical or different, represent a hydrogen atom, a halogen atom, an alkyl group, an alkoxy group, an aryloxy group or the trifluoromethyl group, R represents hydrogen, a cation, an alkyl group, an aryl group or an arylalkyl group, and n is equal to 0 or 1, and their pharmaceutically acceptable salts, useful in the treatment of spasmodic states and allergies.

7 Claims, No Drawings

BENZHYDRYLOXYETHYLPIPERIDINE DERIVATIVES, PROCESS FOR THEIR PREPARATION AND PHARMACEUTICAL COMPOSITIONS, IN WHICH THEY ARE PRESENT

This is a continuation of co-pending application Ser. No. 092,072, filed on Sept. 2, 1987, now abandoned.

The present invention relates to benzhydryloxyethylpiperidine derivatives and their pharmaceutically acceptable salts. It also relates to the processes for the preparation of these derivatives and to the pharmaceutical compositions in which they are present.

The compounds according to the invention, which have valuable pharmacological properties and especially antihistaminic and antispasmodic properties, correspond to one of the formulae below:

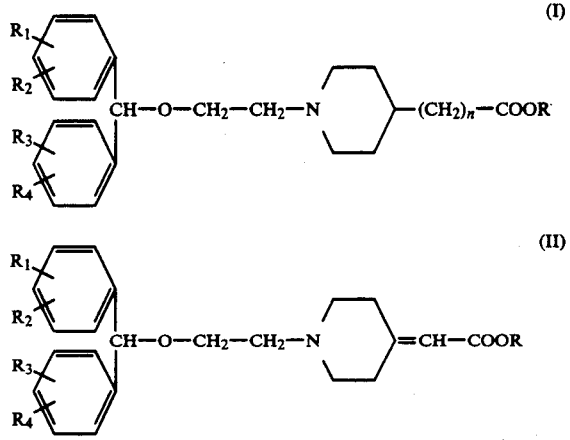

in which:

$R_1$, $R_2$, $R_3$ and $R_4$, which are identical or different, represent a hydrogen atom, a halogen atom, an alkyl group, an alkoxy group, an aryloxy group or the trifluoromethyl group, R represents a hydrogen atom, a cation, an alkyl group, an aryl group or an arylalkyl group, and n is equal to 0 or 1.

For the purposes of the invention, particular preference is given to the following compounds:
ethyl 1-(benzhydryloxyethyl)piperidino-4-acetate,
ethyl 1-(benzhydryloxyethyl)piperidin-4-ylideneacetate and
4-carbethoxy-1-benzhydryloxyethylpiperidine and their pharmaceutically acceptable salts.

For the purposes of the invention, the preferred alkyl groups are aliphatic hydrocarbon radicals containing from 1 to 6 carbon atoms, particular preference being given to the methyl group.

The present also relates to the processes for the preparation of the compounds of the formulae (I) and (II), which are described below:

Process A

Preparation of the compounds of the formula (I)

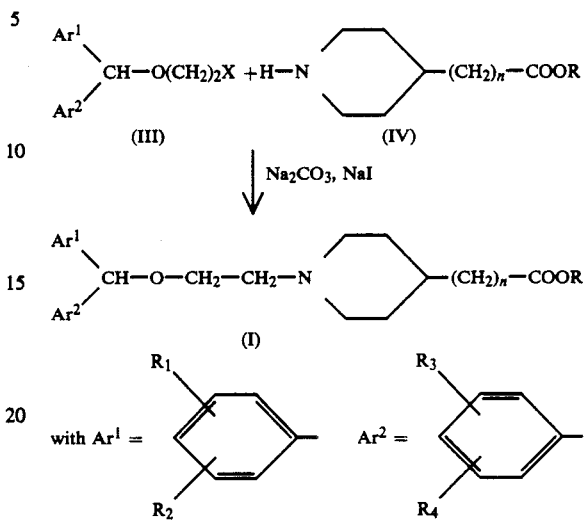

R and n being as defined above.

Process A, represented by the above reaction scheme, consists in refluxing a halogen derivative of the formula (III), in which $Ar^1$ and $Ar^2$ are as defined above and X is a halogen atom, for example chlorine, with an amine of the formula (IV), in which n=0 or 1 and R is as defined above, in an aromatic solvent such as benzene or toluene, or in methyl ethyl ketone, and in the presence of an acceptor for the hydrohalic acid formed. It is advantageous to use sodium or potassium carbonate. A small amount of NaI can be added in order to accelerate the reaction.

The compounds of the general formula (IV) in which n=1 can easily be obtained by the catalytic hydrogenation of the benzyl derivative (V) in solution in an alcohol, for example methanol or ethanol, in the presence of Pd/C at room temperature and pressure:

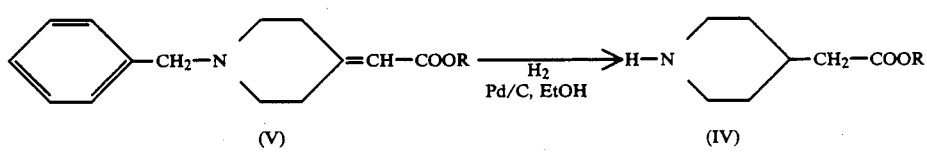

The derivatives of the general formula (V) are obtained by reacting the sodium carbanion of the alkyl diethylphosphonoacetate of the formula (VI) with benzylpiperidone of the formula (VII) in tetrahydrofuran (THF), at 0° C., according to the following equation:

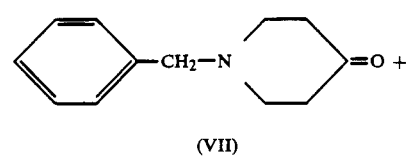

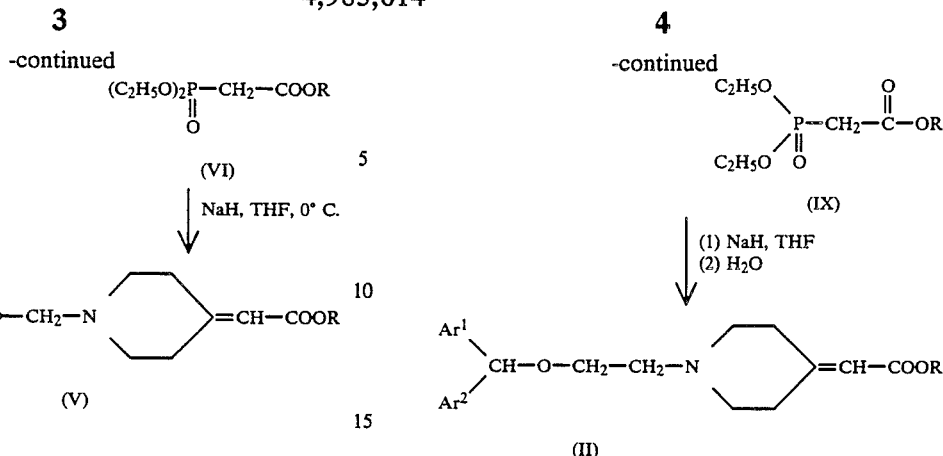

(VI)

NaH, THF, 0° C.

Process B

Preparation of the compounds of the formula (I) in which n=1

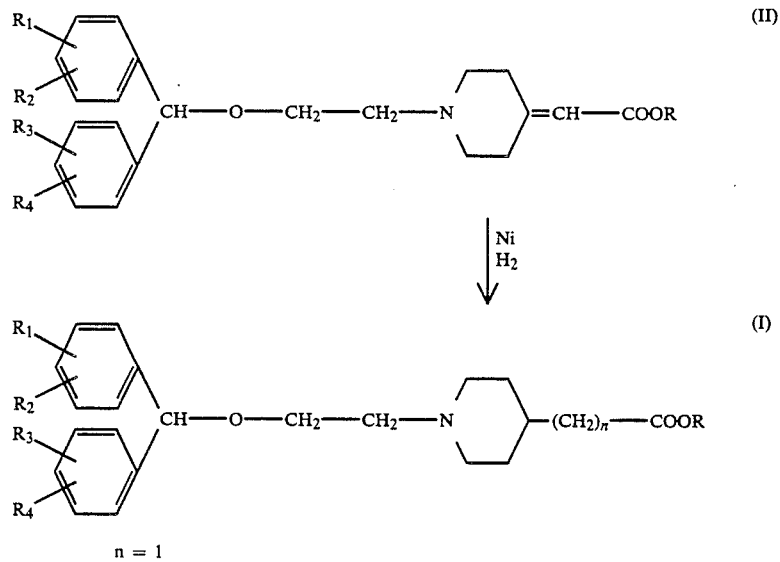

n = 1

According to a modified embodiment of the invention, the compounds of the formula (I) in which n=1 can also be prepared by the catalytic hydrogenation of the corresponding ethylenic compound of the formula (II) in a primary alcohol, for example ethanol or methanol, in the presence of Raney nickel, at room temperature and under hydrogen pressure.

Process C

Preparation of the compounds of the formula (II)

These compounds can be obtained by reacting the sodium carbanion of the alkyl diethylphosphonoacetate (IX) with the benzhydryloxyethylpiperidone (VIII) in tetrahydrofuran (THF) at 0° C.

The general reaction scheme is as follows:

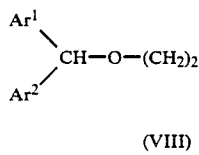

(VIII)

(IX)

(1) NaH, THF
(2) H$_2$O (II)

$Ar^1$, $Ar^2$ and R being as defined above.

The compounds of the formula (VIII) are easily prepared by heating the halogen or tosyl derivatives of the formula (X), in which $Ar^1$ and $Ar^2$ are as defined above, with piperidone hydrochloride (XI), at 80°–90° C., in the presence of two equivalents of sodium carbonate, in a solvent such as dimethylformamide (DMF), according to the method described by L. D. WISE et al. (J. Med. Chem. 1985, 28, 1811–7).

A small amount of NaI can be added in order to accelerate the reaction.

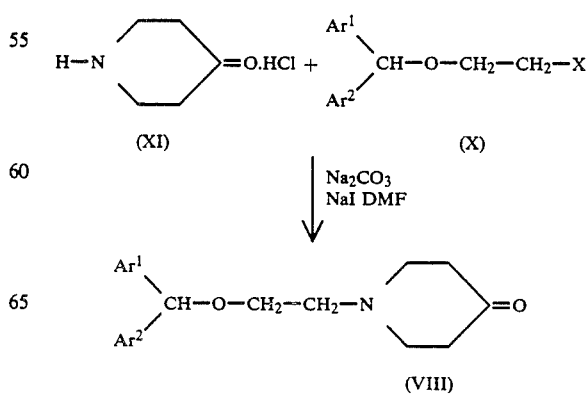

(XI)    (X)

Na$_2$CO$_3$
NaI DMF (VIII)

X = Cl, Br, OTs

The acid addition salts of the derivatives according to the invention can be obtained by conventional processes with acids commonly used to give pharmaceutically acceptable salts, for example acetic acid, hydrochloric acid, hydrobromic acid, methanesulfonic acid, maleic acid, tartaric acid or fumaric acid.

As indicated above, the compounds according to the invention have valuable pharmacological properties and especially antihistaminic and antispasmodic properties, and are particularly suitable for the treatment of spasmodic states and allergies.

The invention therefore also relates to the pharmaceutical compositions in which a derivative according to the invention is present as the active principle, in combination with a pharmaceutically acceptable vehicle.

The compositions according to the invention can be compositions for oral or rectal administration or injectable compositions. They can take the form of solutions, tablets, pills, gelatin capsules, suppositories or injectable compositions.

The invention will now be described in greater detail by means of the illustrative examples below.

The derivatives prepared were identified and characterized by their NMR and infrared spectra and their elemental analysis and are designated in the pharmacological tests by the Applicant's internal references.

EXAMPLE 1

Preparation of 1-(benzhydryloxyethyl)piperidin-4-one (formula VIII: $R_1=R_2=R_3=R_4=H$)

10 g of 1-(benzhydryloxy)-2-chloroethane and 7.65 g of piperidone hydrochloride, dissolved in 200 ml of dimethylformamide, were placed in a 500 ml reactor. 8.52 g of $Na_2CO_3$ and 0.4 g of NaI were added. The mixture was heated at a temperature of 80°-90° C. for 15 hours. After cooling and filtration, the product phase was taken up with 200 ml of water and extracted with 3×50 ml of toluene. The toluene phase was washed with 2×50 ml of 0.1N hydrochloric acid and rendered alkaline with solid $NaHCO_3$ in the presence of 50 ml of water.

After decantation, the organic phase was dried and the solvent was evaporated off to give 11.4 g of a product of the general formula $C_{20}H_{23}NO_2$.

NMR spectrum (solvent $CDCl_3$, reference TMS): 2.3 ppm (m), 4H, $\underline{CH_2}$—C=O; 2.8 ppm (m), 6H, $\underline{CH_2}$—N; 3.5 ppm (t), $2\overline{H}$, $\overline{CH_2}$—O; 5.3 ppm (s), 1H, $CH$—O; 7.1 ppm (m), 10H, $\phi$.

EXAMPLE 2

Preparation of ethyl 1-(benzhydryloxyethyl)piperidin-4-ylideneacetate according to process C (formula II: $R_1=R_2=R_3=R_4=H$; $R=C_2H_5$)

0.6 g of NaH, washed beforehand with 2×5 ml of anhydrous tetrahydrofuran (THF), was placed in a reactor. 50 ml of THF were added, this being followed by the dropwise addition of a solution of ethyl diethylphosphonoacetate in 30 ml of THF at 20° C. The mixture was stirred for 10 min at this temperature.

The mixture was then cooled and the 1-(benzhydryloxyethyl)piperidin-4-one obtained according to Example 1, dissolved in 20 ml of THF, was added slowly at 0° C. The reaction mixture was allowed to return to room temperature and stirred for 2 hours. After evaporation of the solvent, the oil was taken up with 100 ml of water. Extraction was carried out with 3×50 ml of $CH_2Cl_2$, the extract was dried and the solvent was evaporated off to give 8.2 g of a yellow oil of the general formula $C_{24}H_{29}NO_3$.

NMR spectrum (solvent $CDCl_3$, reference TMS): 1.2 ppm (t), 3H, $OCH_2$—$\underline{CH_3}$; 2.5 ppm (m), 10H, $CH_2$—N and $CH_2$—C=; 3.4 ppm (t), 2H, CH—O—$\underline{CH_2}$; 4.0 ppm (q), 2H, C—$\underline{CH_2}$; 5.1 ppm (s), 1H, CH—O; 5.4 ppm (s), 1H, CH=C; 7.0 ppm (m), 10H, $\phi$.

Infrared spectrum: 1610 cm$^{-1}$ (C=C); 1660 cm$^{-1}$ (C=O—).

EXAMPLE 3

Preparation of the maleate of ethyl 1-(benzhydryloxyethyl)piperidino-4-acetate according to process B (formula I: $R_1=R_2=R_3=R_4=H$; $R=C_2H_5$; n=1)

A suspension of 3.52 g of Raney nickel in 80 ml of anhydrous ethanol was placed in an autoclave. 7.6 g of the ethyl 1-(benzhydryloxyethyl)piperidin-4-ylideneacetate (II) obtained according to Example 2 were added. The mixture was hydrogenated under a pressure of 100 kg at room temperature for 24 hours. The catalyst was filtered off and the solvent was evaporated off to give 7.5 g of product.

The maleate was prepared by reacting the oil obtained, dissolved in ether, with a solution of 1.5 g of maleic acid in 2 ml of absolute ethanol. When the addition was complete, the mixture was cooled and filtered to give 9 g of a solid melting at 76° C. and having the empirical formula $C_{24}H_{31}NO_3 \cdot C_4H_4O_4$.

NMR spectrum (base in solution in $CDCl_3$, reference TMS): 1.2 ppm (t), 3H, $CH_3$—C; 1.3 to 2.0 ppm (m), 5H, $CH_2$—C, CH—C; 2.2 ppm (t), 4H, $CH_2N$; 2.6 ppm (t), 2H, $OCH_2$—$CH_2$—N; 2.8 ppm (d), 2H, $\underline{CH_2}$—CO; 3.5 ppm (t), 2H, $\overline{OCH_2}$; 4.0 ppm (q), 2H, $COO\underline{CH_2}$; 5.2 ppm (s), 1H, CHO; 7.0 ppm (m), 10H, $\phi$.

IR spectrum of the salt (1% in KBr): 1730 cm$^{-1}$ (C=O); 1740 cm$^{-1}$ (C=O—); 1590 cm$^{-1}$ (C=C); 2500 cm$^{-1}$ (N+—H).

EXAMPLE 4

Preparation of the fumarate of 4-carbethoxy-1-benzhydryloxyethylpiperidine according to process A (formula I: $R_1=R_2=R_3=R_4=H$; $R=C_2H_5$; n=0)

14 g of 1-benzhydryloxy-2-chloroethane and 8 g of ethyl isonipecotate, dissolved in 140 ml of methyl ethyl ketone, were placed in a reactor. 11.8 g of potassium carbonate and 0.2 g of KI were added.

The mixture was refluxed for 16 hours.

After cooling, the mixture was filtered and the solvents were evaporated off. The viscous oil was taken up with 80 ml of water and extracted with 3×40 ml of $CH_2Cl_2$. The extract was filtered and the solvent was evaporated off to give 18.5 g of product. The fumarate was prepared by reacting the product obtained with a solution of 5.8 g of fumaric acid in 2 ml of anhydrous ethanol. The product was filtered off and dried in an oven to give a solid of the empirical formula $C_{23}H_{29}NO_3 \cdot C_4H_4O_4$. NMR spectrum (base in solution in $CDCl_3$, reference TMS): 1.2 ppm (t), 3H,

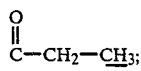

1.8 ppm (m), 4H, CH$_2$—C; 2.1 ppm (m), 1H, CH—COO; 2.6 ppm (m), 6H, CH$_2$N; 3.4 ppm (t), 2H, CH$_2$O; 4.0 ppm (q), 2H, CH$_2$OC=O; 5.2 ppm (s), 1H, CH—O; 7.0 ppm (m), 10H, $\phi$.

EXAMPLE 5

Preparation of ethyl 1-benzylpiperidin-4-ylideneacetate (formula V: R=C$_2$H$_5$; n=1)

A suspension of 7.92 g of NaH in 150 ml of anhydrous THF was placed in a 500 ml reactor. A solution of 73.9 g of ethyl diethylphosphonoacetate in 80 ml of THF was added dropwise at 20° C. The mixture was stirred for 15 min and then cooled to 0° C. A solution of benzylpiperidone (56.7 g) in 80 ml of THF was then added dropwise over a period of 20 min. The reaction mixture was stirred for one hour at room temperature (becoming gelatinous in the process).

The solvent was evaporated off under reduced pressure and the residue was taken up with 150 ml of water. Extraction was carried out with 3×80 ml of CH$_2$Cl$_2$. The extract was acidified to pH 6 with 5% HCl, decanted and dried and the solvent was evaporated off. 61.5 g of an oil were collected and this was used in the crude form in the next example.

NMR spectrum (in solution in CDCl$_3$, reference TMS): 1.2 ppm (t), 3H, COC—CH$_3$; 2.4 ppm (m), 8H, N—(CH$_2$—CH$_2$); 3.4 ppm (s), 2H, $\phi$—CH$_2$; 4.0 ppm (q), 2H, O—CH$_2$—C; 5.5 ppm (s), 1H, CH=C; 7.1 ppm (m), 5H, $\phi$.

EXAMPLE 6

Preparation of ethyl piperidino-4-acetate (formula IV: R=C$_2$H$_5$; n=1)

Ethyl 1-benzylpiperidylideneacetate (21 g) was hydrogenated in solution in absolute ethanol (60 ml), in the presence of 1.6 g of 10% Pd/C and 6.5 ml of a 13N ethanolic solution of hydrochloric acid, at room temperature and pressure.

The catalyst was filtered off and the solvents were evaporated off. The solid was dissolved in 40 ml of water. After neutralization with NaHCO$_3$, extraction was carried out with CH$_2$Cl$_2$ (4×50 ml). The extract was dried and the solvent was evaporated off to give 9.6 g of a product of the general formula C$_9$H$_{17}$NO$_2$.

NMR spectrum (solvent CDCl$_3$, reference TMS): 1.2 ppm (t), 3H, CH$_3$; 1.3 to 3.2 ppm (m), 10H, NH, NCH$_2$—CH$_2$—CH; 2.1 ppm (d), 2H,

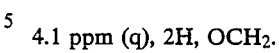

4.1 ppm (q), 2H, OCH$_2$.

EXAMPLE 7

Preparation of ethyl 1-(benzhydryloxyethyl)piperidino-4-acetate (formula I: R$_1$=R$_2$=R$_3$=R$_4$=H; R=C$_2$H$_5$; n=1)

The compound of Example 3 can be obtained according to process A by reacting 1-benzhydryloxy-2-chloroethane of the formula (III) with the ethyl piperidino-4-acetate obtained according to Example 6 above, in toluene, in the presence of potassium carbonate and NaI.

EXAMPLES 8 to 13

The compounds of the formulae (I) and (II) indicated in the table below were obtained by following the procedures described in Examples 2 and 3 above:

TABLE I

| Ex. no. | Derivative of the formula | R$_1$ | R$_2$ | R$_3$ | R$_4$ | n | R | T °C. | Example |
|---|---|---|---|---|---|---|---|---|---|
| 8 | I | H | 4-CH$_3$ | H | H | 1 | C$_2$H$_5$ | 85°(a) | 3 |
| 9 | I | H | 4-Cl | H | H | 1 | C$_2$H$_5$ | (a) | 3 |
| 10 | I | H | 4-CH$_3$ | H | 4-CH$_3$ | 1 | C$_2$H$_5$ | (a) | 3 |
| 11 | II | H | 4-Cl | H | H | — | C$_2$H$_5$ | (b) | 2 |
| 12 | II | H | 4-CH$_3$ | H | 4-CH$_3$ | — | C$_2$H$_5$ | (b) | 2 |
| 13 | II | H | 4-CH$_3$ | H | H | 1 | C$_2$H$_5$ | (a) | 2 |

(a) maleate
(b) fumarate

The NMR spectra of these compounds are given below (solvent CDCl$_3$, reference TMS):

Derivative 8: 1.2 ppm (t), 3H, CH$_3$—C; 1.3 to 2.0 ppm (m), 5H, CH$_2$—C, CH—C; 2.2 ppm (t), 4H, N—CH$_2$—C; 2.3 ppm (s), 1H, CH$_3\phi$; 2.6 ppm (t), 2H, C—CH$_2$—N; 2.8 ppm (d), 2H,

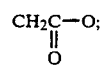

3.5 ppm (t), 2H, O—CH$_2$; 4.0 ppm (q), 2H,

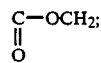

5.2 ppm (s), 1H, CH—O; 7.0 ppm (m), 9H, $\phi$.

Derivative 9: 1.2 ppm (t), 3H, CH$_3$C; 1.3 to 2.0 ppm (m), 5H, CH$_2$—C, CH—C; 2.2 ppm (t), 4H, NCH$_2$C; 2.6 ppm (t), 2H, CCH$_2$—N; 2.8 ppm (d), 2H,

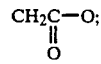

3.5 ppm (t), 2H, OCH$_2$; 4.0 ppm (q), 2H,

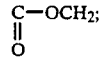

5.2 ppm (s), 1H, CH—O; 7.1 ppm (m), 9H, $\phi$.

Derivative 10: 1.2 ppm (t), 3H, CH₃C; 1.3 to 2.0 ppm, 5H, CH₂—C, CH—C; 2.2 ppm (s), 6H, CH₃φ; 2.2 ppm (t), 4H, N—CH₂—C; 2.6 ppm (t), 2H, C—CH₂—N; 2.8 ppm (d), 2H,

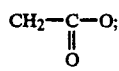

3.5 ppm (t), 2H, OCH₂; 4.0 ppm (q), 2H,

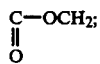

5.2 ppm (s), 1H, CH—O; 7.0 ppm (m), 8H, φ.

Derivative 11: 1.2 ppm (t), 3H, CH₃—C; 2.0 to 3.0 ppm (m), 10H, N—CH₂—CH₂—C, CH₂N; 3.5 ppm (t), 2H, O—CH₂; 4.0 ppm (q), 2H, COOCH₂; 5.2 ppm (s), 1H, CH—O; 5.5 ppm (s), 1H, C=CH; 7.1 ppm (m), 9H, φ.

Derivative 12: 1.2 ppm (t), 3H, CH₃C; 2.1 to 3.1 ppm (m), 10H, C—CH₂CH₂—NCH₂; 2.2 ppm (s), 6H, CH₃φ; 3.5 ppm (t), 2H, OCH₂; 4.0 ppm (q), 2H,

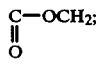

5.1 ppm (s), 1H, CHO; 5.4 ppm (s), 1H,

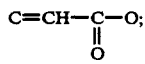

7.0 ppm (m), 8H, φ.

Derivative 13: 1.2 ppm (t), 3H, CH₃—C; 2.0 to 3.2 ppm, 10H, CCH₂CH₂NCH₂; 2.2 ppm (s), 3H, CH₃—φ; 3.5 ppm (t), 2H, OCH₂; 4.0 ppm (q), 2H,

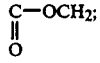

5.2 ppm (s), 1H, CH—O; 5.5 ppm (s), 1H,

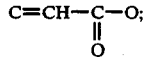

7.1 ppm (m), 9H, φ.

I—TOXICITY TESTS

The toxicity of the compounds of the invention was determined by the following tests:

A. Determination of the 50% lethal dose (LD₅₀) in mice

The derivatives studied were administered intraperitoneally and orally to groups made up of five male mice and five female mice, at a rate of 0.1 ml per ten grams of body weight.

The following doses were used:
for intraperitoneal administration: 100, 150, 200, 300 and 400 mg/kg,
for oral administration: 400, 500, 600, 700, 750 and 800 mg/kg.

The LD₅₀ evaluated from the mortality observed is indicated in Table II below:

TABLE II

| DERIVATIVE | LD₅₀ (i.p.) mg/kg | LD₅₀ (p.o.) mg/kg |
|---|---|---|
| Example 3 (BM 113) | 160 mg/kg | 585 mg/kg |
| Example 2 (BM 138) | 300 mg/kg | |
| Example 4 (BM 159) | 456 mg/kg | |

B. Determination of the minimal lethal dose (MLD) in rats

The derivatives studied were administered intraperitoneally to two groups made up of 5 male rats.
The following doses were used: 75 and 150 mg/kg.
The MLD evaluated from the mortality observed is indicated in Table III below:

TABLE III

| DERIVATIVE | MLD (i.p.) mg/kg |
|---|---|
| Example 3 (BM 113) | 75 mg/kg |

II—PHARMACOLOGICAL TESTS

The pharmacological properties of the compounds of the invention were determined using the following tests:

Experimental protocols

A—Study of the spontaneous motility

The motor activity of mice was determined with the aid of a Boissier and Simon photoelectric actimeter.

The mice are placed in groups of five in a box closed with a lid, through which two perpendicular light rays pass; the mice cut off these rays when they move.

These movements are measured by a counter, which is read after thirty minutes and one hour.

B—Exploration behavior

Thirty minutes after the intraperitoneal administration of the derivatives according to the invention, each mouse is placed on an automated hole-board for five minutes and the number of holes explored is noted every minute.

A 50% effective dose can be calculated from the results obtained.

C—Interaction with the hypermotility caused by dexamphetamine

This test assesses any antagonism of the hyperactivity induced by dexamphetamine administered intraperitoneally at a dose of 3.5 mg/kg.

The mice are placed in groups of five in a Boissier and Simon photoelectric actimeter made up of six boxes closed with a lid, through which two perpendicular light rays pass; the mice cut off these rays when they move.

These movements are measured by a counter, which is read after thirty and sixty minutes.

D—Muscle-relaxing action (traction test)

This test assesses the presence or absence of redressments in a mouse brought up to a horizontal wire with its front paws.

The number of mice which are unable to grip the wire with one of their back paws within five seconds is noted.

A 50% effective dose can be calculated from the results obtained.

E—Interaction with pentobarbital

This test assesses any increase in the sleep induced by pentobarbital which is caused by administering the test product intraperitoneally five minutes before the intraperitoneal injection of pentobarbital (37.5 mg/kg).

A 50% effective dose can be calculated from the results obtained.

F—Peripheral analgesic activity

A peritoneal pain is caused in mice by the intraperitoneal injection of phenylbenzoquinone (PBQ). The test assesses the decrease in the pain syndrome, characterized by an abdominal twisting movement, which is caused by injecting the test product thirty minutes before the administration of PBQ.

The 50% effective dose is calculated from the percentage decrease in the pain syndrome relative to the control animals.

G—Central analgesic activity

This test assesses an increase in the time which is spent on a plate, heated to 60°, by mice treated with the test product thirty minutes before the start of the test.

The 50% effective dose is calculated from the percentage increase in the time spent on the hotplate (licking of the paws or, in some cases, jumping).

H—Interaction with oxotremorine

As oxotremorine is an agonist of cholinergic receptors, substances which antagonize the trembling, hypothermia and peripheral signs (salivation, piloerection) induced by this product can be considered to be anticholinergics.

The test product is administered thirty minutes before the intraperitoneal injection of oxotremorine.

I—Study on an isolated organ (guinea-pig ileum)

This test assesses antagonism towards the contractions induced by histamine hydrochloride in isolated guinea-pig ileum kept at 35° C. in Tyrode's solution.

J—Bronchospasm by inhalation of a histamine solution

Guinea-pigs are placed in a closed chamber into which histamine is introduced as an aerosol, and only those which show very distinct signs of asphyxia within four minutes are selected.

The substance to be studied is administered to groups of guinea-pigs thirty minutes before a further period in the chamber in order to check the resistance to histamine. A guinea-pig is considered to be protected if it resists the histamine aerosol for ten minutes without showing signs of asphyxia.

A 50% effective dose is calculated from the results obtained.

K—Antihistaminic activity

This test assesses the dose which protects fifty per cent of guinea-pigs from a lethal dose of histamine.

The product is administered thirty minutes before the intravenous injection of histamine hydrochloride (1 mg/kg).

The 50% effective dose is calculated from the results obtained.

L—Test for assessing the dose which protects 50% of guinea-pigs from anaphylactic shock This test was carried out according to the following protocol:

Intraperitoneal administration to guinea-pigs of 2 ml of 20% horse serum in physiological solution for three days: D1, D3 and D5.

Trigger action: on D15, oral administration of the test product 45 minutes before the intravenous injection of 0.5 ml of pure horse serum.

An $ED_{50}$ of 0.829 mg/kg (p.o.) was obtained with the compound of Example 3 (BM 113).

Results

The results obtained are collated in Table IV below. These results show that the compounds of the invention have an antihistaminic activity and an antispasmodic activity.

Comparative tests

By way of comparison, the above tests were carried out with Terfenadine as a compound of the prior art; this compound gave the following results in the various tests defined above:

| MICE | |
|---|---|
| Toxicity by intraperitoneal administration | $LD_{50} = 100$ mg·kg$^{-1}$ i.p. |
| Motor activity | Significant decrease at 25 mg·kg$^{-1}$ i.p. |
| Exploration behavior | $ED_{50} = 37$ mg·kg$^{-1}$ i.p. |
| Muscle-relaxing action - traction test | $ED_{50} = 31$ mg·kg$^{-1}$ i.p. |
| Interaction with pentobarbital | $ED_{50} = 25$ mg·kg$^{-1}$ i.p. |
| Peripheral analgesic activity | $ED_{50} = 3.1$ mg·kg$^{-1}$ i.p. |
| GUINEA-PIGS | |
| Bronchospasm by oral administration | $ED_{50} = 1.60$ mg·kg$^{-1}$ p.o. |
| Histaminic shock by oral administration | $ED_{50} = 2.58$ mg·kg$^{-1}$ p.o. |

TABLE IV

| Derivative of the invention | Motor activity (mouse) (mg·kg$^{-1}$ i.p.) | Exploration Behavior (mouse) (mg·kg$^{-1}$ i.p.) | Hypermotility caused by dexamphetamine (mouse) (mg·kg$^{-1}$ i.p.) | Muscle-relaxing action Traction test (mouse) (mg·kg$^{-1}$ i.p.) | Interaction with pentobarbital (mouse) (mg·kg$^{-1}$ i.p.) | Peripheral analgesic activity (mouse) ($ED_{50}$ mg·kg$^{-1}$ i.p.) |
|---|---|---|---|---|---|---|
| Ex. 3 (BM 113) | no modification up to 6.25 | no modification at 25.0 | no modification at 12.5 | no modification at 25.0 | no increase in the sleep induced by pentobarbital | 1.9 |

TABLE IV-continued

| | Central analgesic activity (mouse) | Interaction with oxo-tremorine (mouse) | "In vitro" test (isolated ileum) (ED$_{50}$ µg) | Broncho-spasm (guinea-pig) (ED$_{50}$ mg · kg$^{-1}$) i.p. | Histaminic shock (guinea-pig) (ED$_{50}$ mg · kg$^{-1}$) p.o. | |
|---|---|---|---|---|---|---|
| Ex. 2 (BM 138) | decrease at 11 | no modification at 25.0 | no modification | no modification at 25.0 | increase in the sleep induced by pentobarbital | 1.9 |
| Ex. 4 (BM 159) | no modification | decrease at 25.0 | no modification | no modification | increase at 25.0 | slight analgesia |

| Derivative of the invention | Central analgesic activity (mouse) | Interaction with oxo-tremorine (mouse) | "In vitro" test (isolated ileum) (ED$_{50}$ µg) | Broncho-spasm (guinea-pig) (ED$_{50}$ mg · kg$^{-1}$) i.p. | | Histaminic shock (guinea-pig) (ED$_{50}$ mg · kg$^{-1}$) p.o. |
|---|---|---|---|---|---|---|
| Ex. 3 (BM 113) | no activity | no antagonism | 8.0 | 0.097 | 0.223 | 0.061 |
| Ex. 2 (BM 138) | no activity | no antagonism | >10 | 0.65 | 0.21 | 0.25 |
| Ex. 4 (BM 159) | no activity | no antagonism | 5 | 0.46 | 0.49 | 0.334 |

What is claimed is:

1. Benzhydryloxyethylpiperidine derivatives corresponding to the following formula:

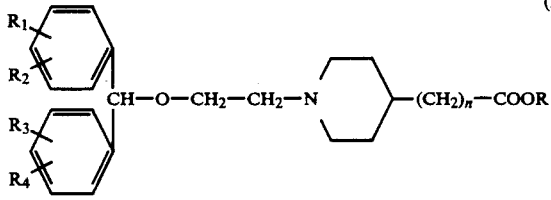

(I)

in which:

R$_1$, R$_2$, R$_3$, and R$_4$, which are identical or different, represent a hydrogen atom, a halogen atom, an alkyl group, an alkoxy group, an aryloxy group or the trifluoromethyl group, R represents hydrogen, a cation, an alkyl group, an aryl group or an arylalkyl group, and n is equal to 0 or 1, and their pharmaceutically acceptable salts.

2. The derivatives as claimed in claim 1 which are:
ethyl 1-(benzyhydryloxyethyl)piperidino-4-acetate, and
4-carbethoxy-1-benzhydryloxyethylpiperidine and their pharmaceutically acceptable salts.

3. Pharmaceutical compositions containing a derivative as claimed in one of claims 1 or 2 as the active ingredient, in combination with a pharmaceutically acceptable vehicle.

4. Benzhydryloxyethylpiperidine derivatives corresponding to the following formula:

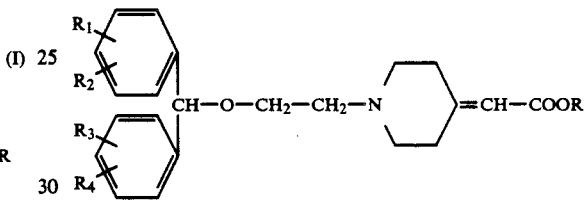

(II)

in which:

—R$_1$, R$_2$, R$_3$, and R$_4$, which are identical or different, represent a hydrogen atom, a halogen atom, an alkyl group, an alkoxy group, an aryloxy group or the trifluoromethyl group, —R represents hydrogen, a cation, an alkyl group, an aryl group or an arylalkyl group, and their pharmaceutically acceptable salts.

5. Pharmaceutical compositions containing a derivative as claimed in claim 4 as the active ingredient, in combination with a pharmaceutically acceptable vehicle.

6. The derivative as claimed in claim 4 which is: -ethyl 1-(benzhydryloxyethyl)piperidin-4-ylideneacetate.

7. Pharmaceutical compositions containing the derivative as claimed in claim 6 as the active ingredient, in combination with a pharmaceutically acceptable vehicle.

* * * * *